United States Patent [19]

Neustadt

[11] Patent Number: 5,208,236
[45] Date of Patent: May 4, 1993

[54] N-(ACYLAMINOMETHYL)GLUTARYL AMINO ACIDS AND USE

[75] Inventor: Bernard R. Neustadt, West Orange, N.J.

[73] Assignee: Schering Corporation, Kenilworth, N.J.

[21] Appl. No.: 950,535

[22] Filed: Sep. 23, 1992

[51] Int. Cl.$^5$ ............... A61K 31/195; A61K 31/535; C07C 275/16; C07D 295/15
[52] U.S. Cl. ............... 514/237.5; 514/482; 514/483; 514/562; 514/563; 544/169; 560/13; 560/25; 560/27; 562/430; 562/439
[58] Field of Search ............... 544/169; 560/27, 25, 560/13; 562/439, 430; 514/237.5, 482, 483, 562, 563

[56] References Cited

U.S. PATENT DOCUMENTS 4,749,688  6/1988  Haslanger et al. ............... 514/19

FOREIGN PATENT DOCUMENTS 274234  12/1987  European Pat. Off.
343911  5/1988  European Pat. Off.
356223  8/1988  European Pat. Off.
358398  8/1989  European Pat. Off.
432898  11/1989  European Pat. Off.
474553  9/1991  European Pat. Off.
481522  10/1991  European Pat. Off.
9108195  11/1923  World Int. Prop. O.
9107378  11/1989  World Int. Prop. O.

OTHER PUBLICATIONS

Erdös, *Hypertension*, 16, 4 (1990) pp. 363–370.
Zimmerman, et al., *Cir. Res.*, 66, 1 (1990), pp. 234–240.
Sybertz, et al., *J. Pharmacol. Exp. Thes.*, 250, 2 (1989), pp. 624–631.
Sybertz, et al., *Hypertension*, 15, 2 (1990), pp. 152–161.
Johnston et al., *Am. J. Med.*, 87, (Suppl. 6) (1989), pp. 245–285.
Gros, et al., *Proc. Nat. Acad. Sci.*, 88, (1991), pp. 4210–4214.

Primary Examiner—Robert W. Ramsuer
Attorney, Agent, or Firm—Paul A. Thompson

[57] ABSTRACT

Novel glutarylamino acid derivative dual inhibitors of neutral endopeptidase and angiotensin converting enzyme of the formula

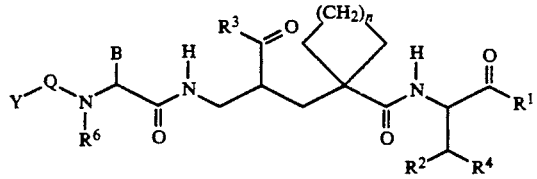

wherein:
$R^1$ and $R^3$ are independently hydroxy, lower alkoxy, aryllower alkoxy, amino, lower alkylamino and di-(lower alkyl)amino;
$R^2$ is H or hydroxy;
$R^4$ is aryl, substituted aryl, heteroaryl or substituted heteroaryl;
$R^6$ is H or $R^7$—$(CH_2)_3$—, wherein $R^7$ is amino or (aryllower alkoxy)carbonylamino;
Q is —C(O)— or —SO$_2$—;
Y is lower alkyl, lower alkoxy, aryllower alkoxy, amino, lower alkylamino, di-(lower alkyl)amino, or a group of the formula

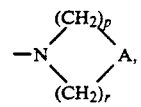

wherein A is a bond, —N(R$^5$)—, or —O—; and R$^5$ is H or lower alkyl;
B is H or Z—(CH$_2$)$_m$—
Z is amino, lower alkylamino, di-(lower alkyl)amino, (aryllower alkoxy)carbonylamino, 1-pyrrolidino or 1-piperidino;
m=1,2,3,4 or 5; and n=1,2 or 3; or or a pharmaceutically acceptable addition salt thereof; useful in the treatment of cardiovascular disorders, are disclosed.

11 Claims, No Drawings

N-(ACYLAMINOMETHYL)GLUTARYL AMINO ACIDS AND USE

BACKGROUND OF THE INVENTION

The present invention relates to N-(acylaminomethyl)glutaryl amino acids which are dual inhibitors of neutral endopeptidase and angiotensin converting enzyme, useful in the treatment of cardiovascular disorders.

Cardiovascular disorders which may be treated with compounds of the present invention include hypertension, congestive heart failure and renal insufficiency.

The renin-angiotensin system is a complex hormonal system comprised of a large molecular weight precursor, angiotensinogen, two processing enzymes, renin and angiotensin converting enzyme (ACE), and a vasoactive mediator, angiotensin II (A II). The enzyme renin catalyzes the cleavage of angiotensinogen into the decapeptide angiotensin I (A I), which has minimal biological activity on its own and is converted into the active octapeptide A II by ACE. A II has multiple biological actions on the cardiovascular system, including vasoconstriction, activation of the sympathetic nervous system, stimulation of aldosterone production, antinatriuresis, stimulation of vascular growth and stimulation of cardiac growth. A II functions as a pressor hormone and is involved in the pathophysiology of several forms of hypertension.

Angiotensin converting enzyme (ACE) is a zinc-metalloprotease which converts A I to A II. Inhibitors of this enzyme, which have been widely studied, include the drugs captopril, enalapril, lisinopril and spirapril. Although a major mode of action of ACE inhibitors involves prevention of formation of the vasoconstrictor peptide A II, it has been reported in *Hypertension*, 16, 4(1990) p. 363-370 that ACE cleaves a variety of peptide substrates, including the vasoactive peptides bradykinin and substance P. Prevention of the degradation of bradykinin by ACE inhibitors has been demonstrated, and the activity of the ACE inhibitors in some conditions has been reported in *Circ. Res.*, 66, 1 (1990) p. 242-248 to be mediated by elevation of bradykinin levels rather than inhibition of A II formation.

Neutral endopeptidase (EC 3.4.24.11; enkephalinase; atriopeptidase; NEP) is a zinc-containing metalloprotease which cleaves a variety of peptide substrates on the amino terminal side of aromatic amino acids. Substrates for this enzyme include, but are not limited to, atrial natriuretic factors (ANF), brain natriuretic peptide, met and leu enkephalin, bradykinin, neurokinin A, and substance P.

Inhibitors of NEP lower blood pressure and exert ANF-like effects such as diuresis and increased cyclic guanosine 3',5'-monophosphate (cGMP) excretion in some forms of experimental hypertension. The antihypertensive action of NEP inhibitors is mediated through ANF since antibodies to ANF will neutralize the reduction in blood pressure.

U.S. Pat. No. 4,749,688 established the antihypertensive action of NEP inhibitors and that co-administration of an ACE inhibitor and a NEP inhibitor results in a greater reduction of blood pressure than observed with either agent alone. The antihypertensive effect is best manifested under conditions in which the renin-angiotensin system is suppressed, as reported by Sybertz et al in *J. Parmacol. Exp. Ther.*, 250, 2 (1989) pp. 624-631 and in *Hypertension*, 15, 2 (1990) pp. 152-161. For example, NEP inhibitors reduce blood pressure effectively in the desoxycorticosterone salt (DOCA) hypertensive rat, a volume-dependent, renin-suppressed model of hypertension, but are less effective under conditions in which the renin-angiotensin system is activated, such as in the spontaneously hypertensive rat (SHR) and in the two kidney Goldblatt hypertension model. Studies in the SHR and in the two-kidney Goldblatt hypertension model using a prodrug of the NEP inhibitor N-[2(S)-mercaptomethyl-3-(2-methylphenyl)propionyl]-methionine in combination with the ACE inhibitor spirapril demonstrated the greater efficacy of the combination compared to either drug alone. However, this interaction was inhibited in SHR which had been nephrectomized, a manipulation which markedly suppresses renin levels.

An explanation of this interactive effect of ACE inhibitors and NEP inhibitors on blood pressure is that suppression of the renin angiotensin system allows for full expression of the ANF-like antihypertensive effect of the NEP inhibitor. A II and ANF exert opposite effects on the cardiovascular system and it has been proposed by Johnston et al in *Am. J. Med.*, 87, (Suppl 6) (1990) p. 24S-28S that these two hormonal systems act to counterbalance one another.

Compounds possessing dual activity as NEP-ACE inhibitors have been reported. European Patent Publication EP 0358398 discloses cycloalkyl-substituted glutaramides of the formula

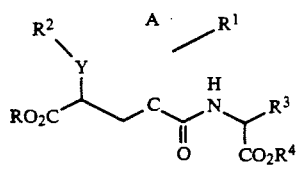

wherein: A completes a 5 or 6 membered carbocyclic ring; $R^1$ is H or alkyl; R and $R^4$ are H, alkyl, cycloalkyl, benzyl or an alternative biolabile ester-forming group; Y is a bond or an alkylene group; $R^2$ is H, aryl, heterocyclyl, or a carboxamido, carbamoyl, sulfamoyl or sulfonamido group; and $R^3$ is a group of the formula

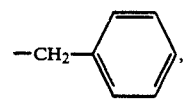

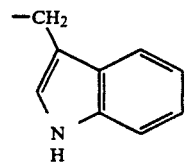

or

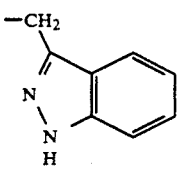

wherein the benzene ring of said group is optionally substituted;

European Patent Publication EP 0474553 discloses actinoin derivatives of the formula

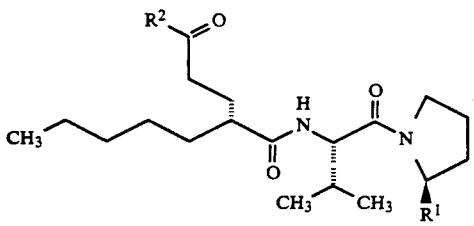

wherein $R^1$ is sulfoxymethyl, carboxyl, carboxamido, hydroxyaminocarbonyl or alkoxycarbonyl; and $R^2$ is hydroxy, alkoxy, hydroxyamino or sulfoxyamino;

European Patent Publication EP 0481522 discloses compounds of the formula

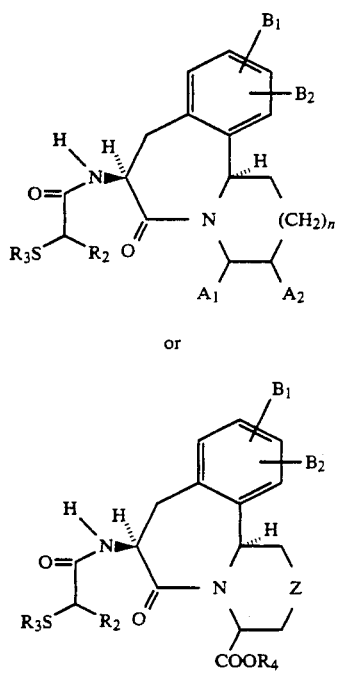

wherein:
A$_1$ and A$_2$ are independently H or —COOR$_4$; provided that where A$_1$ is H, A$_2$ is —COOR$_4$, and where A$_1$ is —COOR$_4$, A$_2$ is H;
B$_1$ and B$_2$ are independently H, OH, C$_1$-C$_4$ alkoxy, aryl or aryl(C$_1$-C$_4$ alkyl); or, where B$_1$ and B$_2$ are attached to adjacent carbon atoms, B$_1$ and B$_2$ together with the carbons to which they are attached comprise a benzene or methylenedioxy ring;
R$_2$ is H, C$_1$-C$_8$ alkyl, —CH$_2$—O—(CH$_2$)$_2$—O—CH$_3$, aryl or aryl(C$_1$-C$_4$ alkyl);
R$_3$ is H, acetyl, —CH$_2$—O—C(O)—CCH$_3$, or benzoyl;
R$_4$ is H, —CH$_2$—O—C(O)—CCH$_3$, C$_1$-C$_4$ alkyl, diphenylmethyl, aryl or aryl(C$_1$-C$_4$ alkyl); and
n is 0 or 1;

having activity as inhibitors of both neutral endopeptidase and angiotensin converting enzyme; and Gros, et al., *Proc. Natl. Acad. Sci.* USA, 88, (1991) pp 4210–4214, discloses dual inhibitors of ACE and NEP of the formula

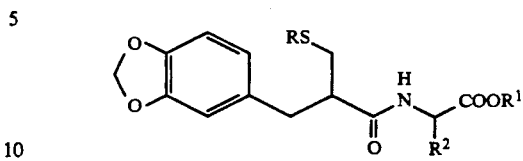

wherein R is H or CH$_3$C(O)—, R$^1$ is H or benzyl, and R$^2$ is H or methyl.

SUMMARY OF THE INVENTION

Novel compounds of the present invention are represented by the formula I

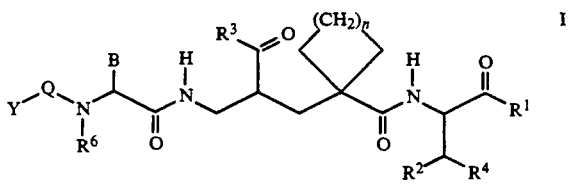

wherein:
R$^1$ and R$^3$ are independently selected from the group consisting of hydroxy, lower alkoxy, aryllower alkoxy, amino, lower alkylamino and di-(lower alkyl)amino;
R$^2$ is H or hydroxy;
R$^4$ is aryl, substituted aryl, heteroaryl or substituted heteroaryl;
R$^6$ is H or R$^7$—(CH$_2$)$_3$—, wherein R$^7$ is amino or (aryllower alkoxy)carbonylamino;
Q is —C(O)— or —SO$_2$—;
Y is lower alkyl, lower alkoxy, aryllower alkoxy, amino, lower alkylamino, di-(lower alkyl)amino, or a group of the formula

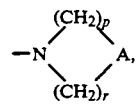

wherein A is a bond, —N(R$^5$)—, or —O—; p and r are independently 2 or 3; and wherein R$^5$ is H or lower alkyl;
B is H or Z—(CH$_2$)$_m$—
Z is amino, lower alkylamino, di-(lower alkyl)amino, (aryllower alkoxy)carbonylamino, (lower alkoxy)carbonylamino,

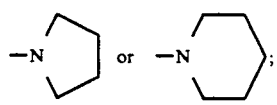

m=1,2,3,4 or 5; and
n=1,2 or 3; or
or a pharmaceutically acceptable addition salt thereof.

Preferred are compounds of the formula I wherein R$^1$ and R$^3$ are hydroxy, R$^2$ is H, and R$^4$ is aryl or substituted aryl.

More preferred are compounds of the formula I having the chemical structure

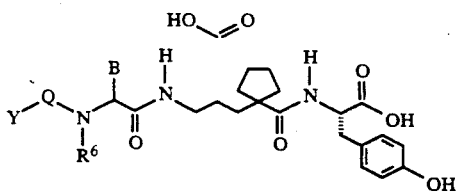

wherein B, Y, Q and $R^6$ are as defined above.

Most preferred are compounds of the formula I having the chemical structure

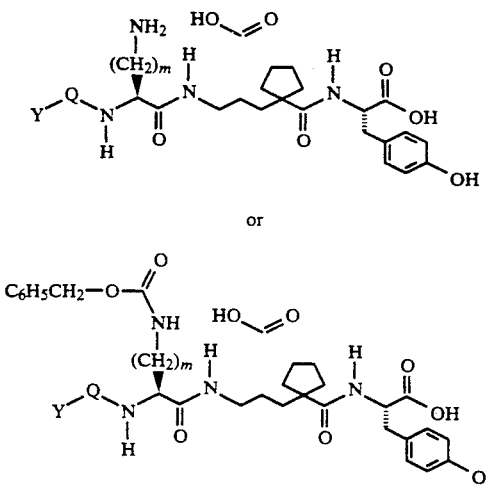

wherein Q is —C(O)— or —$SO_2$—, and Y is lower alkoxy, di-(lower alkyl)amino or a group of the formula

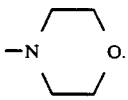

Another group of most preferred compounds are compounds of the formula I having the chemical structure

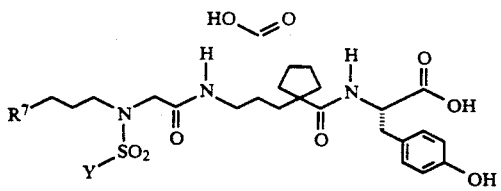

wherein Y is lower alkyl, and $R^7$ is as defined above.

DETAILED DESCRIPTION

As used herein, the definitions of the following terms are applicable:

"lower alkyl" means straight or branched alkyl chains of 1 to 6 carbon atoms, and "lower alkoxy" similarly refers to alkoxy groups having 1 to 6 carbon atoms;

"halogeno" means a fluorine, chlorine, bromine or iodine radical;

"aryl" means phenyl or naphthyl;

"substituted aryl" means an aryl group bearing 1 to 3 substituents selected from the group consisting of lower alkyl, hydroxy, lower alkoxy, lower alkylthio, halogeno, trifluoromethyl, phenyl, phenoxy, phenylthio, di-(lower alkyl)amino, acylamino, perfluoroacylamino, carbamoyl, lower alkylaminocarbonyl, sulfamoyl, lower alkanesulfonylamino or perfluoro(lower alkane)sulfonylamino;

"heteroaryl" means indolyl, indazolyl, or benzofuranyl; and

"substituted heteroaryl" means a heteroaryl group bearing 1 to 3 substituents selected from the group consisting of lower alkyl, hydroxy, lower alkoxy, lower alkylthio, halogeno, trifluoromethyl, phenyl, phenoxy, phenylthio, di-(lower alkyl)amino, acylamino, perfluoroacylamino, carbamoyl, lower alkylaminocarbonyl, sulfamoyl, lower alkanesulfonylamino or perfluoro(lower alkane)sulfonylamino.

Certain compounds of the invention are acidic, e.g., those compounds which possess a carboxyl group. These compounds form pharmaceutically acceptable salts with inorganic and organic bases. Examples of such salts are the sodium, potassium and calcium salts. Also included are salts formed with pharmaceutically acceptable amines such as ammonia, alkyl amines, hydroxyalkylamines, N-methylglucamine and the like.

The salts may be formed by conventional means, as by reacting the free acid form of the product with one or more equivalents of the appropriate base in a solvent or medium in which the salt is insoluble, or in a solvent such as water which is then removed in vacuo or by freeze-drying or by exchanging the cations of an existing salt for another cation on a suitable ion exchange resin.

Certain compounds of the invention, e.g. those compounds which possess an amino, lower alkylamino or di-(lower alkyl)amino group, also form pharmaceutically acceptable salts with organic and inorganic acids. Examples of suitable acids for such salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, $K_2CO_3$, $NH_3$ and $NaHCO_3$. The free base forms differ from their respective salt forms somewhat in certain physical properties, such as solubility in polar solvents, but the salts are otherwise equivalent to their respective free base forms for purposes of this invention.

Compounds of the formula I have at least one asymmetrical carbon atom and therefore include various stereoisomers. The invention includes all such isomers both in pure form and in admixture, including racemic mixtures.

The following solvents and reagents employed in preparing compounds of the present invention are identified by the abbreviations indicated: diethyl ether ($Et_2O$); ethyl acetate (EtOAc); methanol (MeOH); ethanol (EtOH); dimethylformamide (DMF); tetrahydrofuran (THF); acetic acid (AcOH); 1-(3-dimethylaminopropyl)-3-ethylcarbodiimide hydrochloride (EDCl); dicyclohexylcarbodiimide (DCC); 1-hydroxybenzotriazole hydrate (HOBT); trifluoroacetic acid (TFA); and the abbreviation Cbz as used herein represents a benzyloxycarbonyl group.

Compounds of the present invention can be prepared via methods known to those skilled in the art. For example, compounds of formula I can be prepared by coupling an amine of the formula II with a carboxylic acid of the formula III, in the presence of a coupling agent, such as EDCI or DCC, an activating agent, such as HOBT, and a suitable solvent, such as DMF.

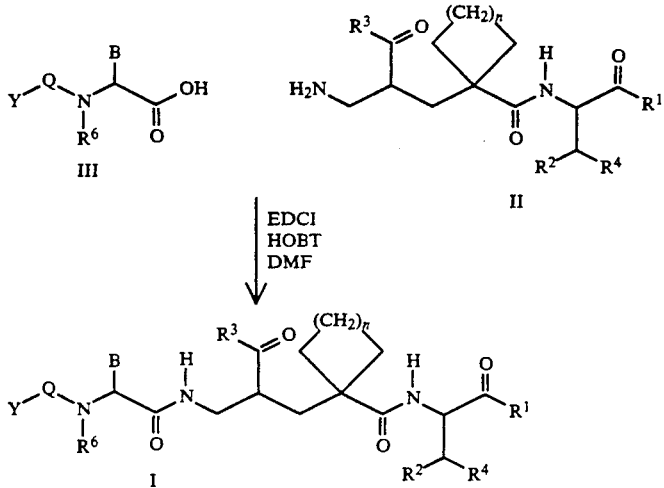

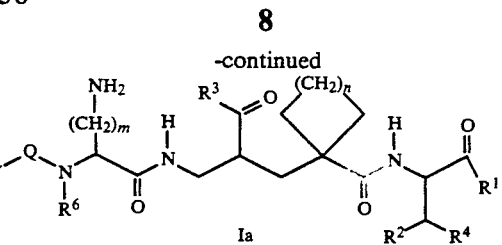

In another method, compounds of the formula Ia, i.e., compounds of the formula I wherein B is Z—$(CH_2)_m$— and Z is amino, can be prepared by hydrogenation of a compound of the formula Ib, i.e., a compound of the formula I wherein B is Z—$(CH_2)_m$— and Z is (arylmethoxy)carbonylamino, in a suitable solvent, such as MeOH or EtOH, in the presence of a suitable hydrogenation catalyst, e.g. palladium on carbon, preferably 10% Pd on carbon.

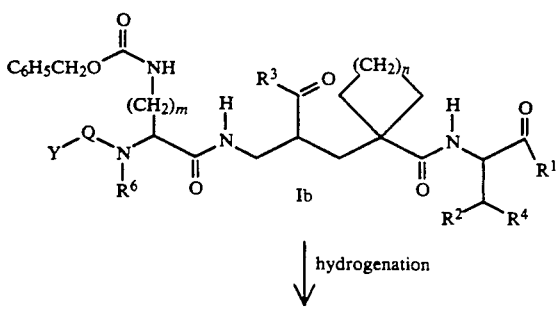

In a third method, compounds of the formula Ic, i.e., compounds of the formula I wherein $R^1$ and $R^3$ are hydroxy, can be prepared from compounds of the formula Id, i.e., compounds of the formula I wherein $R^1$ and $R^3$ are t-butoxy, by treating with an appropriate acid, such as TFA.

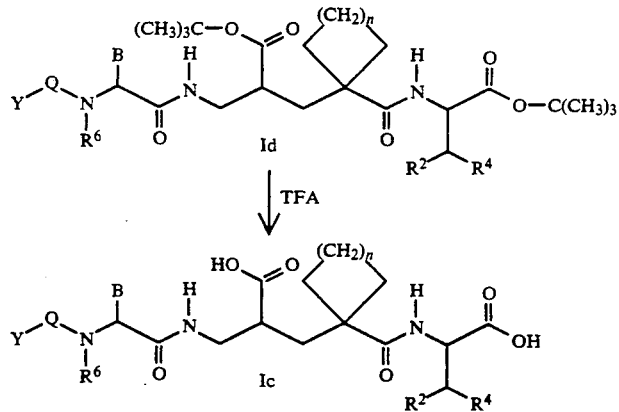

Compounds of the formula III are commercially available or can be prepared by methods well known in the art. For example, compounds of the formula IIIa, i.e., compounds of the formula III wherein B is Z—$(CH_2)_4$—, Z is (aryllower alkoxy)carbonylamino, Q is —C(O)—, and Y is lower alkoxy, can be prepared by reacting an amino acid of the formula IV with a lower alkyl chloroformate, such as methyl chloroformate, in a suitable solvent, such as THF, in the presence of an aqueous base, such as 1N NaOH.

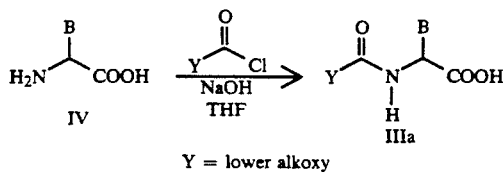

Y = lower alkoxy

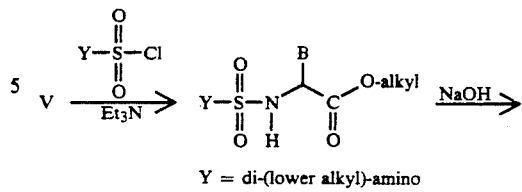

Y = di-(lower alkyl)-amino

Compounds of the formula IIIb, i.e., compounds of the formula III wherein B is Z—(CH₂)₄—, Z is (aryllower alkoxy)carbonylamino, Q is —C(O)—, and Y is di-(lower alkyl)amino or a group of the formula

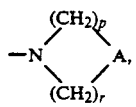

as defined above, can be prepared by reacting an amino ester of the formula V with a carbonyl chloride of the formula VII, preferably dimethylaminocarbonyl chloride or 4-morpholinecarbonyl chloride, in the presence of a tertiary amine base, such as triethylamine, optionally in the presence of a suitable solvent, such as CH₂Cl₂, to give the urea derivative VI, which is treated with an aqueous base, such as 1N NaOH, in a suitable solvent, such as a lower alkyl alcohol, preferably EtOH, to give a compound of the formula IIIb.

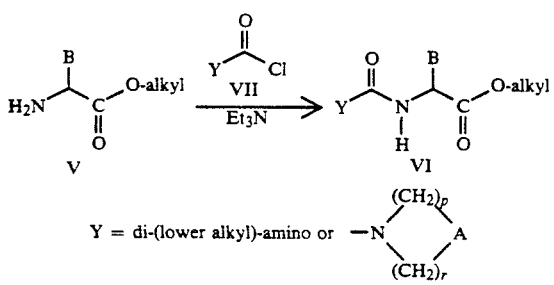

Y = di-(lower alkyl)-amino or 

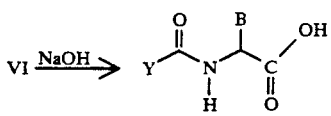

Y = di-(lower alkyl)-amino or 

Compounds of the formula IIIc, i.e., compounds of the formula III wherein R⁶ is H, Q is —SO₂—, Y is di-(lower alkyl)amino, can be prepared by treating an amino ester of the formula V, as defined above, with a di-(lower alkyl)sulfamoyl chloride, e.g. dimethylsulfamoyl chloride, in the presence of a tertiaryamine base, such as triethylamine, followed by hydrolyzing the resulting ester of the formula VIII by treating with an aqueous base, such as 1N NaOH, in a suitable solvent, such as a lower alkyl alcohol, preferably EtOH, to obtain the desired compound IIIc.

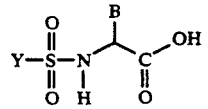

Y = di-(lower alkyl)-amino

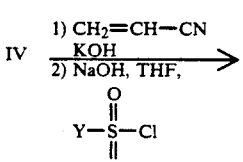

Y = di-(lower alkyl)-amino

Compounds of the formula IIId, i.e., compounds of the formula III wherein R⁶ is R⁷—(CH₂)₃—, Q is —SO₂—, and Y is lower alkyl, can be prepared from amino acids of the formula IV, as defined above, by reacting the amino acid with acrylonitrile, in the presence an aqueous base, such as KOH in water, followed by treating with a lower alkanesulfonyl chloride, such as methanesulfonyl chloride, in a suitable solvent, e.g. THF, in the presence of an aqueous base such as 1N NaOH, to give the nitrile IX. The nitrile is hydrogenated in the presence of a suitable hydrogenation catalyst, e.g. Raney nickel, in aqueous ammonia, and the resulting amine X, reacted with an (aryllower alkyl) chloroformate, such as benzyl chloroformate, in a suitable solvent, such as THF, in the presence of an aqueous base, such as 1N NaOH, to obtain a compound of the formula IIId.

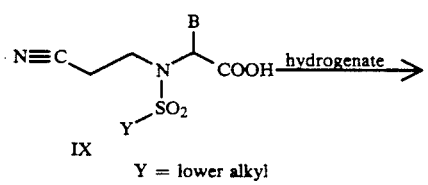

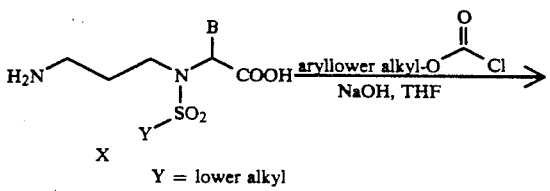

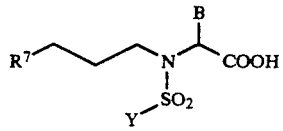

IIId Y = lower alkyl
R⁷ = (aryllower alkoxy)-carbonylamino

Compounds of the formula II can be prepared by the methods disclosed in EP 358398 and EP 432898.

Compounds of the formula IV, V and VII are commercially available or can be prepared by methods well known in the art.

The ACE inhibitory activity of the compounds of the present invention is determined via in vitro tests using standard test procedures for ACE inhibition well known to those skilled in the art. Similarly, NEP inhibitory activity is determined via in vitro tests using standard test procedures for NEP inhibition well known to those skilled in the art.

The antihypertensive effects of dual inhibitors of the present invention are determined according to the following procedures.

DOCA Salt Model

For the DOCA salt hypertension model, male Sprague Dawley rats weighing 100–150 g are anesthetized with ether and the right kidney is removed. Three pellets containing Doc acetae (desoxycorticosterone acetate, DOCA, 25 mg/pellet) are implanted subcutaneously. Animals recover from surgery, are maintained on normal rat chow and are allowed free access to a fluid of 1% NaCl and 0.2% KCl instead of tap water for a period of 25–30 days. This procedure results in a sustained elevation in blood pressure and is a slight modification of published procedures (e.g. Brock et al, 1982) that have been used to produce DOCA salt hypertension in the rat.

On the day of the study, animals are again anesthetized with ether and the caudal artery is cannulated for blood pressure measurement. Patency of the caudal artery cannula is maintained with a continuous infusion of dextrose in water at a rate of 0.2 mL/hr. Animals are placed into restraining cages where they recover consciousness. Blood pressure is measured from the caudal artery catheter using a Statham pressure transducer attached to a Beckman oscillographic recorder. In addition, a cardiovascular monitoring device (Buxco Electronics, Inc.) and a digital computer are used to calculate average blood pressures.

After an equilibration period of at least 1.5 hr., animals are dosed subcutaneously (1 mL/kg) with vehicle (methylcellulose, hereinafter MC) and dual NEP-ACE inhibitor, and blood pressure is monitored for the next 4 hours.

A1 Challenge Assay

Male Sprague-Dawley rats weighing 270–345 g are anesthetized with ether and the abdominal aorta cannulated via the caudal (ventral tail) artery with polyethylene tubing (PE10 fused to PE50). A jugular vein is also cannulated with polyethylene tubing and both cannulae exteriorized at the back of the neck. The catheters are filled with heparinized saline (0.2%) and sealed. Animals are fasted overnight, then placed into plastic restrainers. Blood pressure is recorded from the arterial catheter. Patency of the arterial cannula is maintained by a continuous infusion of 5% dextrose in water at a rate of 0.2 mL/hr.

After a 30 min. stabilization period, animals are challenged with angiotensin I (AI) and angiotensin II (AII) (0.3 $\mu$g/kg dissolved in physiological saline solution and injected iv in volumes of 100 $\mu$L/kg followed by 100 $\mu$L flush) twice at 5–10 min. intervals during a control period. The glutarylamino acids are then administered orally (via a feeding needle) in 0.4% aqueous methylcellulose vehicle in a volume of 2 mL/kg. AI and AII challenges are repeated at 30 min. intervals for the next 6 hr.

FSHR Assay

Male spontaneously hypertensive rats (SHR), 16–18 weeks old, are pretreated via oral gavage with 50 mg/kg of furosemide (in a volume of 4 mL/kg) the evening before the day of testing. The rats are fasted overnight, but have ad libitum access to water, and are pretreated with furosemide (as before) the morning before surgical preparation on the day of testing. The pretreated rats are anesthetized with ether, the caudal (ventral tail) artery cannulated with polyethylene tubing ($PE_{50}$), and their blood pressure and heart rate recorded. The rats are placed in plastic cages to recover.

After a 90 minute stabilization period, the glutarylamino acids are administered orally as solutions or suspensions in 0.4% aqueous methylcellulose vehicle via a feeding needle. The amino acid or vehicle is given in a volume of 4 mL/kg.

Alternatively, the glutarylamino acids (0.4%) dissolved or suspended in a vehicle composed of 10% (v/v) ethanol, 20% 0.1N (tris[hydroxymethyl]-aminoethane) and 70% methylcellulose, are administered via a subcutaneous (sc) route. A volume of 2 mL/kg is used to deliver the drug or vehicle in these sc studies.

ANF has been shown to exert beneficial hemodynamic and renal actions in congestive heart failure (CHF) with the exception of the most severe states, in which its actions may be blunted. ANF and the renin angiotensin system also act as physiological antagonists of one another in CHF. Therefore, it is contemplated that a dual NEP-ACE inhibitor will be useful in the treatment of CHF. Measurements of the degree of diuresis and natriuresis, as well as hemodynamics, are used to determine the efficacy of the present combination in the treatment of CHF.

A variety of pharmaceutical dosage forms are suitable, preferably for oral or parenteral administration, although mechanical delivery systems such as transdermal dosage forms are also contemplated.

The daily dosages of the compounds of this invention for treatment of hypertension or congestive heart failure are about 0.3 mg/kg to about 100 mg/kg of mammalian weight per day administered in single or divided doses. The exact dose to be administered is determined by the attending clinician and is dependent on the potency of the compound administered, the age, weight, condition and response of the patient.

Generally, in treating humans having hypertension or congestive heart failure, the compounds of this invention can be administered in dosage ranges of about 1.0 to 50 mg/kg.

Typical oral formulations include tablets, capsules, syrups, elixirs and suspensions. Typical injectable formulations include solutions and suspensions.

The typical pharmaceutically acceptable carriers for use in the formulations described above are exemplified by: sugars such as lactose, sucrose, mannitol and sorbitol; starches such as cornstarch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate; polyvinylpyrrolidone; polyvinyl alcohol; stearic acid; alkaline earth metal stearates such as magnesium stearate and calcium stearate; stearic acid; vegetable oils such as peanut oil, cottonseed oil, sesame oil, olive oil and corn oil; non-ionic, cationic and anionic surfactants; ethylene glycol polymers; betacyclodextrin; fatty alcohols; and hydrolyzed cereal solids, as well as other non-toxic compatible fillers, binders, disintegrants, buffers, preservatives, antioxidants, lubricants, flavoring agents, and the like commonly used in pharmaceutical formulations.

Following are illustrative examples of procedures for preparing compounds of formula I.

PREPARATION 1

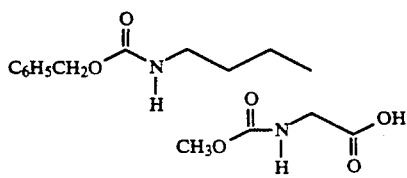

Add ε-Cbz-L-lysin (2.80 g, 10.0 mmol) in 1.0N NaOH (30 mL) dropwise to a solution of methyl chloroformate (1.41 g, 15 mmol) in THF (10 mL). Stir for 4 h., acidify with 1.0N HCl, and extract with EtOAc. Dry the extract over MgSO$_4$, filter and concentrate to obtain the title compound.

PREPARATION 2

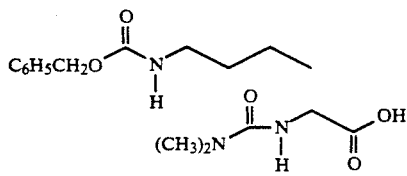

Step A: To ε-Cbz-L-lysine ethyl ester (3.08 g, 10.0 mmol) and triethylamine (1.51 g, 15 mmol) in CH$_2$Cl$_2$ (30 mL) add dropwise dimethylcarbamoyl chloride (1.61 g, 15 mmol). Stir the mixture for 4 days, concentrate to a residue, and partition the residue between EtOAc and 1.0N HCl. Dry the EtOAc solution over MgSO$_4$, filter and concentrate to obtain the product:

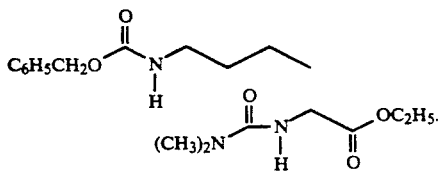

Step B: Treat the product of step A (3.5 g, 9.2 mmol) in EtOH (100 mL) with 1.0N NaOH (30 mL). After 2 h., concentrate to a residue and partition the residue between EtOAc and 1.0N HCl. Dry the EtOAc solution over MgSO$_4$, filter and concentrate to a residue. Partition the residue between CH$_2$Cl$_2$ and water, dry the CH$_2$Cl$_2$ solution and concentrate to give the title compound.

PREPARATION 3

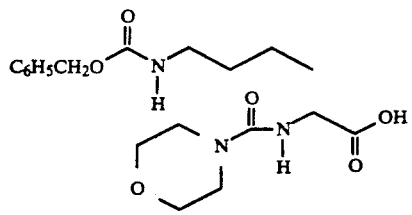

Step A: To a mixture of ε-Cbz-L-lysine ethyl ester (3.08 g, 10.0 mmol) and triethylamine (1.51 g, 15 mmol) add 4-morpholinecarbonyl chloride (2.24 g, 15 mmol). Stir the mixture for 18 h., then partition between EtOAc and 1.0N HCl. Dry the EtOAc solution over MgSO$_4$, filter, and concentrate to a residue. Chromatograph the residue (60–200 silica gel, 3% MeOH/CH$_2$Cl$_2$) to obtain the product:

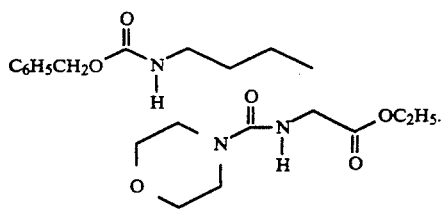

Step B: Treat the product of step A (3.5 g, 8.3 mmol) in EtOH (25 mL) with 1.0N NaOH (23 mL) for 2 h., then concentrate to a residue. Partition the residue between EtOAc and 1.0N HCl, wash the EtOAc solution with water, then dry over MgSO$_4$. Concentrate to give the title compound.

PREPARATION 4

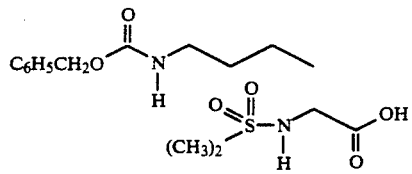

Step A: To a mixture of ε-Cbz-L-lysine ethyl ester (3.08 g, 10.0 mmol) and triethylamine (1.51 g, 15 mmol) add dimethylsulfamoyl chloride (2.15 g, 15 mmol) and stir for 3 days. Partition between EtOAc and water, dry the EtOAc solution over MgSO$_4$, filter and concentrate to a residue. Chromatograph the residue (60–200 silica gel, 5% MeOH/CH$_2$Cl$_2$) to obtain the product:

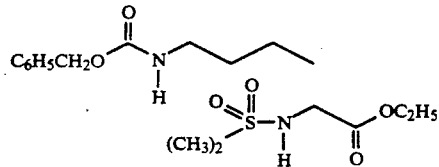

Step B: Treat the product of step A (3.0 g, 7.2 mmol) in EtOH (10 mL) with 1.0N NaOH (28 mL) for 2 h., then concentrate to a residue. Partition the residue between EtOAc and 1.0N HCl, wash the EtOAc solution with water, dry over MgSO$_4$ and concentrate to a residue. Repeat treatment with 1.0N NaOH (20 mL) for 18 h., then work up as before to give the title compound.

PREPARATION 5

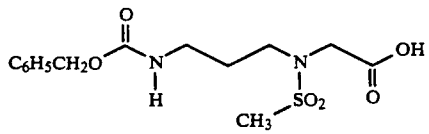

Step A: Cool a solution of glycine (3.8 g, 50 mmol) and KOH (3.3 g, 50 mmol) in water (50 mL) to 0° C., then add dropwise acrylonitrile (2.8 g, 53 mmol). Allow the mixture to warm to room temperature and stir 18 h.

Add 1.0N NaOH (100 mL) and cool to 0° C., then add methanesulfonyl chloride (8.6 g, 74 mmol) in THF (40 mL) dropwise and stir for 2 h. Acidify with concentrated HCl to pH=1, and saturate with NaCl. Extract with EtOAc, dry the extract over MgSO$_4$, filter and concentrate to obtain the product:

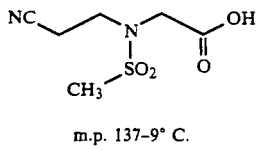

m.p. 137-9° C.

Step B: Combine the product of step A (3.0 g, 15 mmol) and Raney nickel (3.6 g) in concentrated NH$_4$OH (150 mL), and hydrogenate at 50 psi for 0.5 h. Filter, treat with charcoal, and filter to obtain the product:

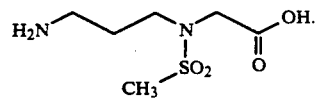

Step C: To a solution of the product of step B (3.1 g, 15 mmol) in 1.0N NaOH (45 mL), add benzyl chloroformate (3.7 g, 22 mmol) in THF (20 mL) dropwise, then stir for 2 h. Concentrate to remove THF, wash with Et$_2$O, add 1.0N HCl (60 mL), and extract with EtOAc. Dry the EtOAc extract over MgSO$_4$, filter and concentrate to give the title compound, m.p. 74°-6° C.

EXAMPLE 1

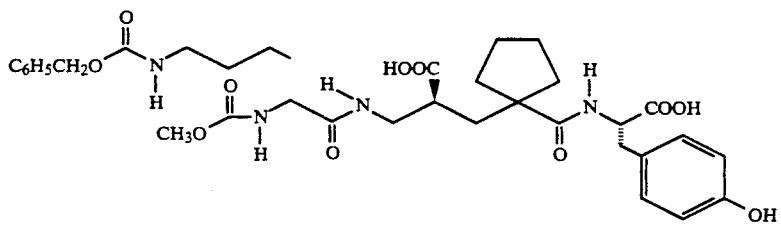

Step A: Combine the product of Preparation 1 (0.43 g, 1.28 mmol), HOBT (0.19 g, 1.28 mmol), and N-[1-[3-amino-2(S)-t-butoxycarbonylpropyl]cyclopentanecarbonyl]-L-(O-t-butyl)tyrosine t-butyl ester (0.70 g, 1.28 mmol) in dry DMF (20 mL). Add EDCl (0.29 g, 1.53 mmol) and stir for 18 h. Partition between EtOAc and water and wash the EtOAc solution with 1.0N NaHCO$_3$, then water. Dry over MgSO$_4$, filter and concentrate to a residue. Chromatograph the residue (60-200 silica, 3% MeOH/CH$_2$Cl$_2$) to obtain N-[1-[3-N$^2$-methoxycarbonyl-N$^6$-phenylmethoxycarbonyl-L-lysylamino]-2(S)-t-butoxycarbonylpropyl]cyclopentanecarbonyl]-L-(O-t-butyl)tyrosine t-butyl ester, $[\alpha]_D^{21} = +3.3°$ (EtOH).

Step B: Dissolve the product of step A (0.95 g, 1.1 mmol) in TFA (50 mL) and allow to stand for 2 h. Concentrate to a residue, and partition the residue between EtOAc and water. Wash the EtOAc solution with water, dry over MgSO$_4$, filter and concentrate to give the title compound, $[\alpha]_D^{22} = +6.4°$ (EtOH).

Using substantially the same procedure, the following compounds can be prepared:

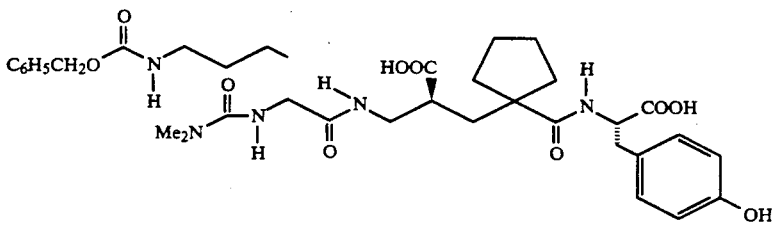

1A $[\alpha]_D^{22} = +6.7°$
(EtOH)

-continued
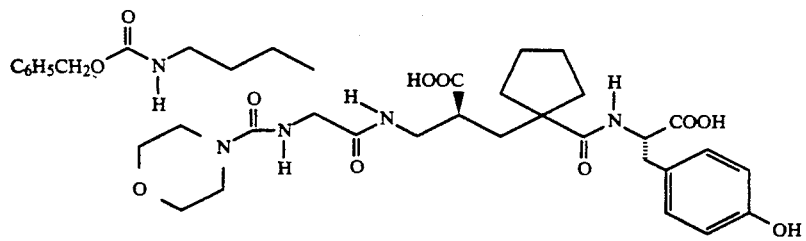
1B
$[\alpha]_D^{22} = +5.2°$
(EtOH)
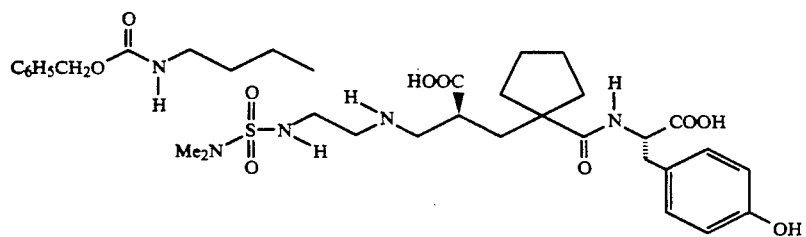
1C
$[\alpha]_D^{22} = +5.4°$
(EtOH)
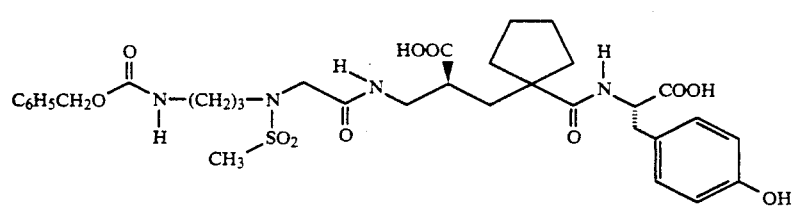
1D
$[\alpha]_D^{22} = +15.3°$
(EtOH)
EXAMPLE 2
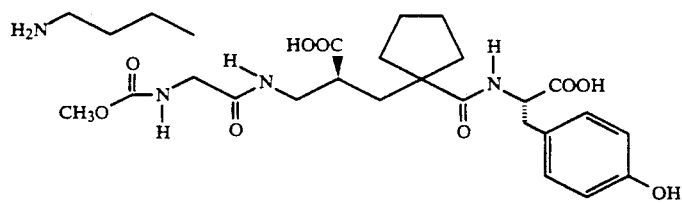
Hydrogenate the product of Example 1 (0.30 g, 0.42 mmol) in MeOH (75 mL) over with 10% Pd on carbon (0.4 g) at 50 psi for 2 h. Filter and concentrate to give the title compound, $[\alpha]_D^{22} = +14.8°$ (EtOH).
Using substantially the same procedure, the following compounds can be prepared:
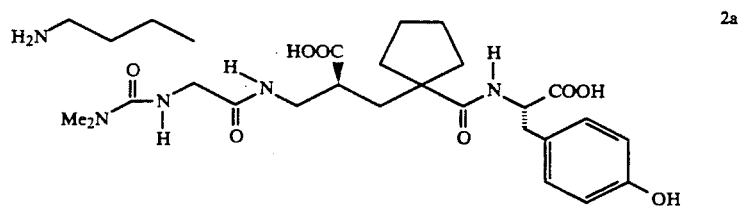
2a
$[\alpha]_D^{22} = +3.6°$
(EtOH—CH$_2$Cl$_2$)

-continued

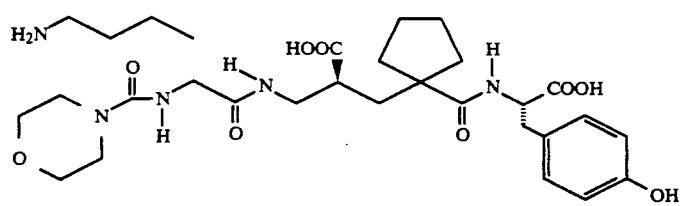

2B

MS (M+H) 796

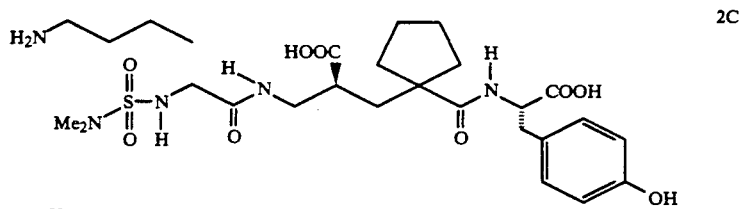

2C

[α]$D^{22}$ = +6.5°
(EtOH)

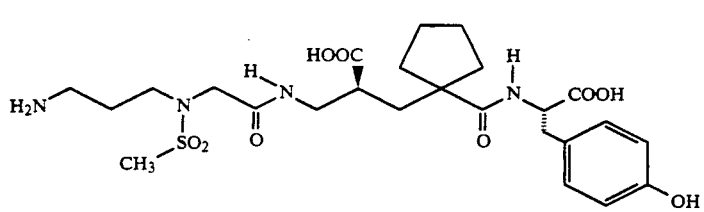

2d

[α]$D^{22}$ = +19.4°
(EtOH)

Using the methods described above, the following activity data were obtained for compounds of the formulae shown in the following tables. Changes in BP are expressed as mm Hg (dose) and A1 Challenge data are expressed as % inhibition (dose).

| Z | Q | Y | IC$_{50}$, nM | | Change in BP | | A1 Chall. |
|---|---|---|---|---|---|---|---|
| | | | NEP | ACE | DOCA | FSHR | |
| Cbz—NH— | —C(O)— | CH$_3$O— | 8 | 15 | 18 (10 po) | 2 (10 sc) | 49% (30 sc) |
| NH$_2$— | —C(O)— | CH$_3$O— | 33 | 60 | 63 (10 sc) 46 (10 po) | 35 (10 sc) | 92% (30 sc) |
| Cbz—NH— | —C(O)— | (CH$_3$)$_2$NH— | 2 | 450 | 34 (10 sc) | 13 (10 sc) | 88% (30 sc) |
| NH$_2$— | —C(O)— | (CH$_3$)$_2$NH— | 1 | 15 | 41 (10 sc) 25 (10 po) | 60 (10 sc) 6 (3 po) | |
| Cbz—NH— | —C(O)— | ![morpholine] | 2 | 2 | 4 (10 po) | 17 (10 sc) | |
| NH$_2$— | —C(O)— | ![morpholine] | 9 | 8 | 28 (10 po) | 52 (10 sc) | |
| Cbz—NH— | —SO$_2$— | (CH$_3$)$_2$NH— | 1 | 1 | | 18 (10 sc) | |
| NH$_2$— | —SO$_2$— | (CH$_3$)$_2$NH— | 32 | | 22 (10 po) | 49 (10 SC) | |

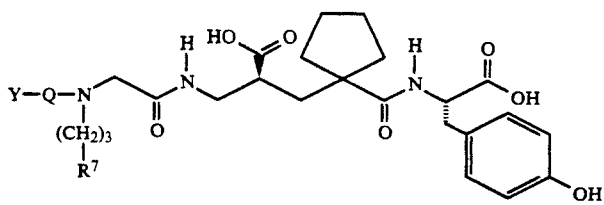

| R[7] | Q | Y | IC$_{50}$, nM | | Change in BP | | A1 Chall. |
|---|---|---|---|---|---|---|---|
| | | | NEP | ACE | DOCA | FSHR | |
| Cbz—NH— | —SO$_2$— | CH$_3$— | 2 | 40 | 4 (12 po) | 16 (10 sc) | 100% (10 sc) |
| NH$_2$— | —SO$_2$— | CH$_3$— | 1 | 6 | 12 (10 sc) | 12 (10 sc) | 81% (30 sc) |
| | | | | | 12 (10 po) | | |

I claim:
1. A compound having the structural formula

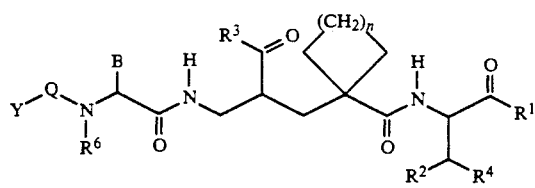

wherein:
R[1] and R[3] are independently selected from the group consisting of hydroxy, lower alkoxy, aryllower alkoxy, amino, lower alkylamino and di-(lower alkyl)amino;
R[2] is H or hydroxy;
R[4] is aryl, substituted aryl, heteroaryl or substituted heteroaryl;
R[6] is H or R[7]—(CH$_2$)$_3$—, wherein R[7] is amino or (aryllower alkoxy)carbonylamino;
Q is —C(O)— or —SO$_2$—;
Y is lower alkyl, lower alkoxy, aryllower alkoxy, amino, lower alkylamino, di-(lower alkyl)amino, or a group of the formula

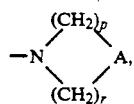

wherein A is a bond, —N(R[5])—, or —O—; p and r are independently 2 or 3; and wherein R[5] is H or lower alkyl;
B is H or Z—(CH$_2$)$_m$—
Z is amino, lower alkylamino, di-(lower alkyl)amino, (aryllower alkoxy)carbonylamino, (lower alkoxy)-carbonylamino

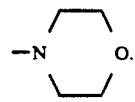

m=1,2,3,4 or 5; and
n=1,2 or 3; or
or a pharmaceutically acceptable addition salt thereof.
2. A compound of claim 1 wherein R[1] and R[3] are hydroxy, R[2] is H, and R[4] is aryl or substituted aryl.
3. A compound of claim 2 wherein n=2 and R[4] is 4-hydroxyphenyl.
4. A compound of claim 3 having the structural formula

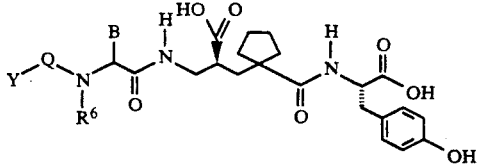

wherein B, Y, Q and R[6] are as defined in claim 1.
5. A compound of claim 4 wherein B is Z—(CH$_2$)$_m$—, and Z is amino or (aryllower alkoxy)carbonylamino.
6. A compound of claim 5 wherein R[6] is H, and Y is lower alkoxy, di-(lower alkyl)amino or a group of the formula 7. A compound of claim 4 wherein B is H, Q is —SO$_2$—, and R[6] is R[7]—(CH$_2$)$_3$—.
8. A compound of claim 7 wherein Y is lower alkyl.
9. A compound of claim 1 having the structural formula

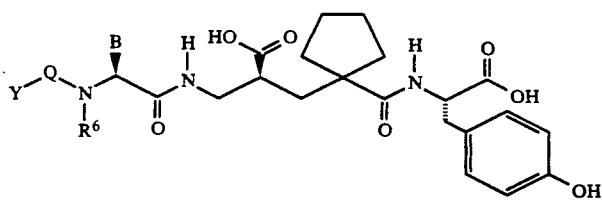

| Compound | B | wherein R⁶ | Q | Y |
|---|---|---|---|---|
| 1 | Cbz—NH—(CH₂)₄— | H | —C(O)— | CH₃O— |
| 2 | NH₂—(CH₂)₄— | H | —C(O)— | CH₃O— |
| 1A | Cbz—NH—(CH₂)₄— | H | —C(O)— | (CH₃)₂NH— |
| 2A | NH₂—(CH₂)₄— | H | —C(O)— | (CH₃)₂NH— |
| 1B | Cbz—NH—(CH₂)₄— | H | —C(O)— | morpholino |
| 2B | NH₂—(CH₂)₄— | H | —C(O)— | morpholino |
| 1C | Cbz—NH—(CH₂)₄— | H | —SO₂— | (CH₃)₂NH— |
| 2C | NH₂—(CH₂)₄— | H | —SO₂— | (CH₃)₂NH— |
| 1D | H | NH₂—(CH₂)₃— | —SO₂— | CH₃— |
| 2D | H | Cbz—NH—(CH₂)₃— | —SO₂— | CH₃— |

10. A pharmaceutical composition useful for treating hypertension, congestive heart failure or renal insufficiency comprising an effective amount of a compound of claim 1 in a pharmaceutically acceptable carrier.

11. A method of treating hypertension, congestive heart failure or renal insufficiency comprising administering to a mammal in need of such treatment a pharmaceutical composition of claim 10.

* * * * *